US010134130B2

(12) United States Patent
Sugiura et al.

(10) Patent No.: US 10,134,130 B2
(45) Date of Patent: Nov. 20, 2018

(54) MAGNETIC-RESONANCE IMAGING APPARATUS, MEDICAL IMAGE-PROCESSING APPARATUS, AND IMAGE PROCESSING METHOD

(71) Applicant: Toshiba Medical Systems Corporation, Otawara-shi (JP)

(72) Inventors: Takamasa Sugiura, Kawasaki (JP); Taichiro Shiodera, Shinagawa (JP); Tomoyuki Takeguchi, Kawasaki (JP); Yasunori Taguchi, Kawasaki (JP); Naotaka Sakashita, Utsunomiya (JP); Masao Yui, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/337,493

(22) Filed: Oct. 28, 2016

(65) Prior Publication Data
US 2017/0124707 A1 May 4, 2017

(30) Foreign Application Priority Data

Oct. 30, 2015 (JP) .................................. 2015-215237

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/7203* (2013.01); *G01R 33/48* (2013.01);
(Continued)

(58) Field of Classification Search
CPC .......... G01R 33/5608; G01R 33/56536; G06T 5/005; G06T 5/50; G06T 7/0012; G06T 2207/10088
See application file for complete search history.

(56) References Cited

U.S. PATENT DOCUMENTS

| 7,782,051 B2 * | 8/2010 | Haacke | G01R 33/56536 324/307 |
| 7,949,384 B2 * | 5/2011 | Lewin | G01R 33/022 324/306 |

(Continued)

OTHER PUBLICATIONS

Ferdinand Schweser et al., Quantitative imaging of intrinsic magnetic tissue properties using MRI signal phase: An approach to in vivo brain iron metabolism?, 2010 Elsevier Inc. pp. 2789-2807.*

(Continued)

*Primary Examiner* — Mekonen Bekele
(74) *Attorney, Agent, or Firm* — Oblon, McClelland, Maier & Neustadt, L.L.P.

(57) ABSTRACT

A magnetic-resonance imaging apparatus of an embodiment includes acquiring circuitry and processing circuitry. The acquiring circuitry acquires a magnetic resonance signal that is generated from a subject. The processing circuitry creates a phase image based on the magnetic resonance signal. The processing circuitry sets a combination of a plurality of filters that are used to remove a phase variation derived from a background magnetic field according to a region in the phase image. The processing circuitry removes a phase variation derived from the background magnetic field from the phase image by using the combination of the filters.

12 Claims, 13 Drawing Sheets

(51) Int. Cl.
*A61B 5/055* (2006.01)
*A61B 5/00* (2006.01)
*G06T 5/20* (2006.01)
*G01R 33/48* (2006.01)

(52) U.S. Cl.
CPC ............ *G06T 5/20* (2013.01); *A61B 2576/00* (2013.01); *G06T 2207/10088* (2013.01)

(56) References Cited

U.S. PATENT DOCUMENTS

| | | | | |
|---|---|---|---|---|
| 9,165,386 | B2* | 10/2015 | Sato | A61B 5/055 |
| 9,709,641 | B2* | 7/2017 | Sato | G01R 33/243 |
| 2008/0154119 | A1* | 6/2008 | Lewin | G01R 33/022 |
| | | | | 600/410 |
| 2009/0261824 | A1* | 10/2009 | Haacke | G01R 33/56536 |
| | | | | 324/307 |
| 2011/0044524 | A1* | 2/2011 | Wang | G01R 33/54 |
| | | | | 382/131 |
| 2012/0049846 | A1* | 3/2012 | Gross | G01R 33/565 |
| | | | | 324/309 |
| 2013/0221961 | A1* | 8/2013 | Liu | G01R 33/56545 |
| | | | | 324/307 |
| 2015/0002148 | A1* | 1/2015 | Liu | A61B 5/055 |
| | | | | 324/309 |
| 2015/0310639 | A1* | 10/2015 | Bilgic | G01R 33/243 |
| | | | | 382/131 |
| 2017/0108570 | A1* | 4/2017 | Eichner | G01R 33/56545 |

OTHER PUBLICATIONS

Ferdinand Schweser, et al., "Quantitative imaging of intrinsic magnetic tissue properties using MRI signal phase: An approach to in vivo brain iron metabolism" NeuroImage, vol. 54, No. 4, 2011, pp. 2789-2807.

* cited by examiner

FIG.4A
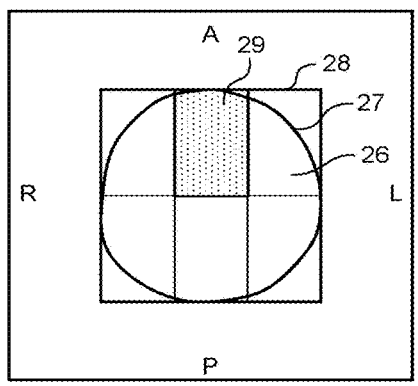
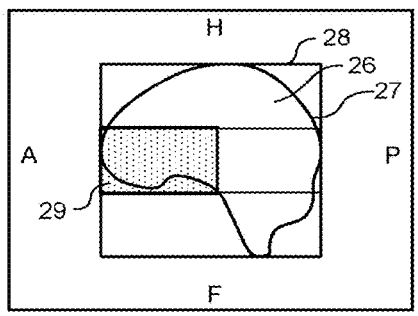
FIG.4B
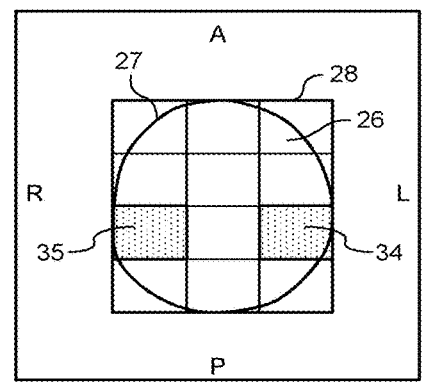
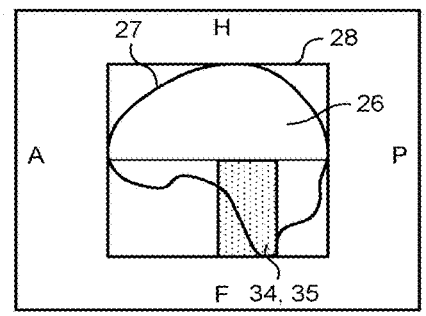

FIG.4C
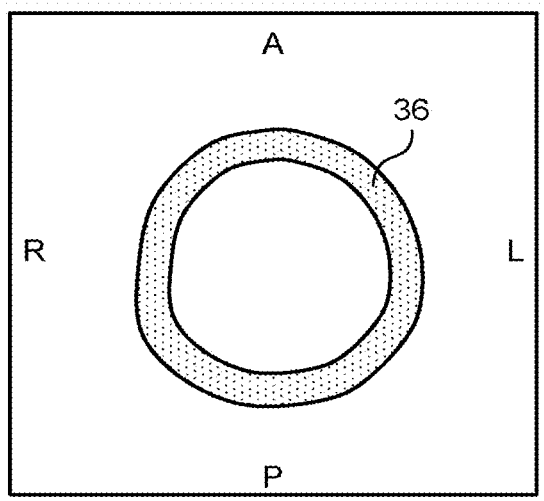
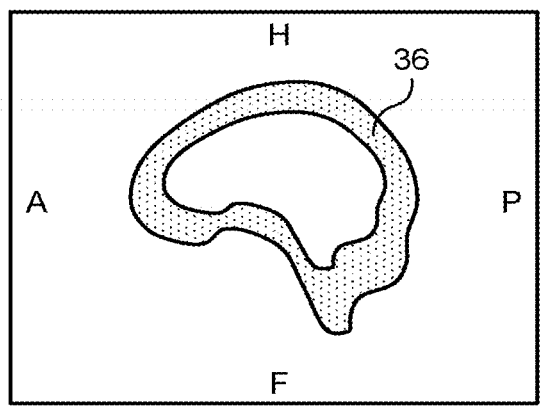

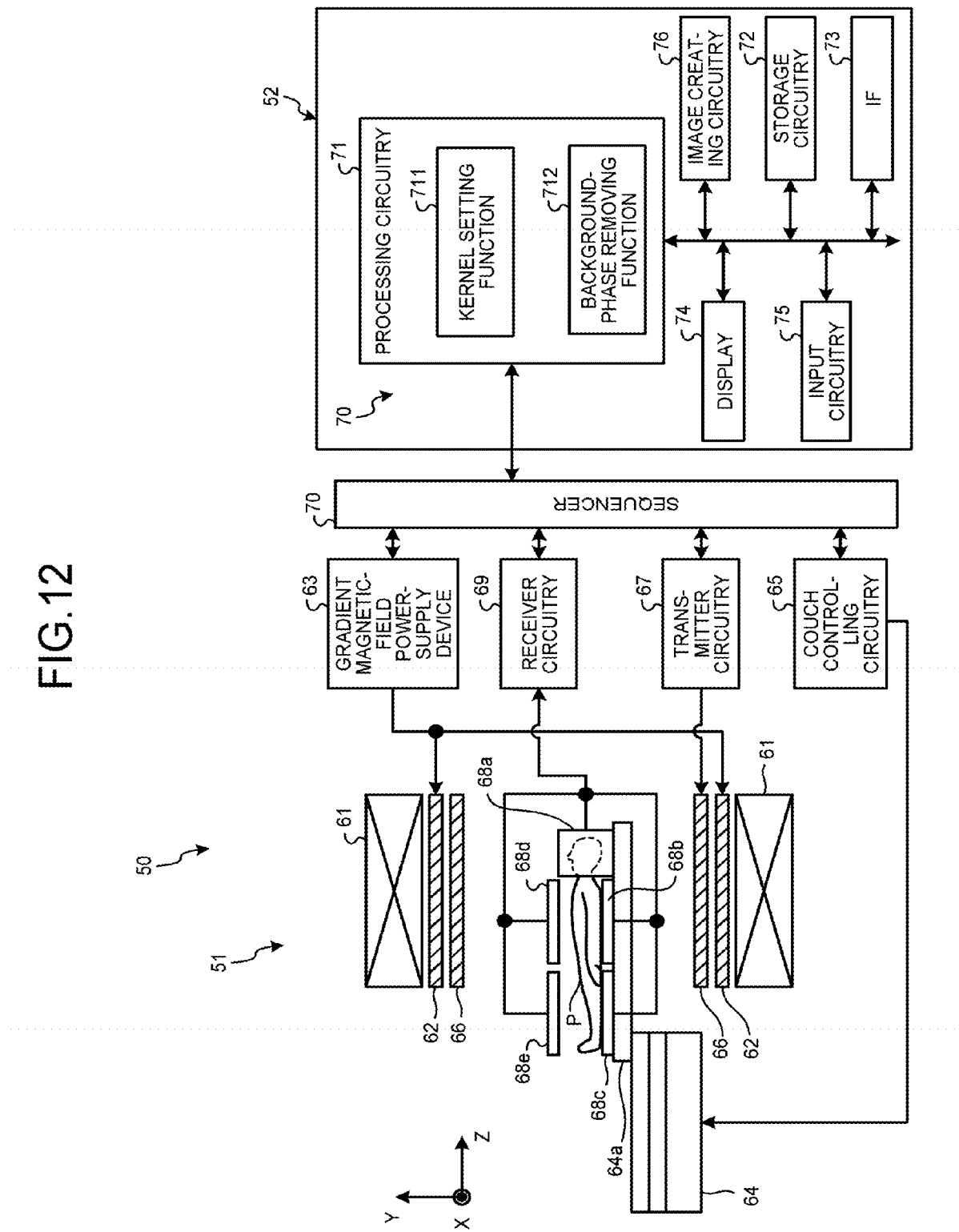

MAGNETIC-RESONANCE IMAGING APPARATUS, MEDICAL IMAGE-PROCESSING APPARATUS, AND IMAGE PROCESSING METHOD

CROSS-REFERENCE TO RELATED APPLICATIONS

This application is based upon and claims the benefit of priority from Japanese Patent Application No. 2015-215237, filed on Oct. 30, 2015; the entire contents of which are incorporated herein by reference.

FIELD

Embodiments described herein relate generally to a magnetic-resonance imaging apparatus, a medical image-processing apparatus, and an image processing method.

BACKGROUND

Magnetic-resonance imaging (MRI) apparatuses magnetically excite the nuclear spin of a subject that is placed in a static magnetic field by high frequency pulses of the Larmor frequency, and generate an image from magnetic resonance (MR) signals that occur with the excitation. The generated image includes an intensity image expressing an intensity of an MR signal, and a phase image expressing a phase. The phase image includes information about magnetic susceptibility of a tissue, and by using this, susceptibility weighted imaging (SWI) to create image contrast emphasizing the magnetic susceptibility, and quantitative susceptibility mapping (QSM) to measure magnetic susceptibility quantitatively are performed.

BRIEF DESCRIPTION OF THE DRAWINGS

FIG. 4A depicts a peripheral area of a paranasal sinus;

FIG. 4B depicts a peripheral area of temporal lobes;

FIG. 4C depicts a peripheral area of boundaries of a brain;

FIG. 12 is a schematic diagram of an MRI apparatus according to a third embodiment.

DETAILED DESCRIPTION

A magnetic-resonance imaging apparatus of an embodiment includes acquiring circuitry and processing circuitry. The acquiring circuitry acquires a magnetic resonance signal that is generated from a subject. The processing circuitry creates a phase image based on the magnetic resonance signal. The processing circuitry sets a combination of a plurality of filters that are used to remove a phase variation derived from a background magnetic field according to a region in the phase image. The processing circuitry removes a phase variation derived from the background magnetic field from the phase image by using the combination of the filters.

The magnetic-resonance imaging apparatus and a medical image-processing apparatus according to embodiments are explained in detail below. Respective embodiments and modifications can be combined appropriately.

First Embodiment

Figure 1:
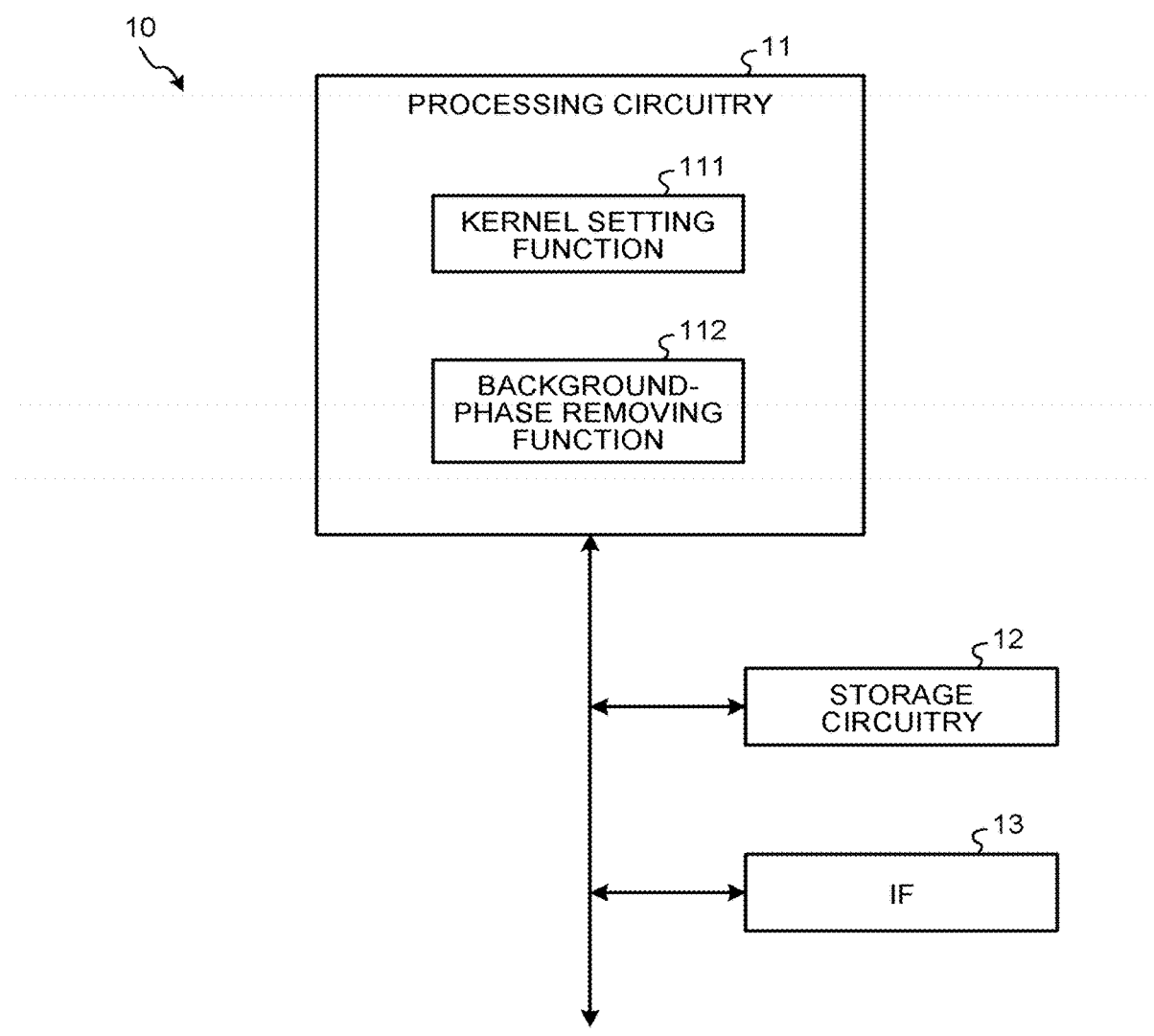
FIG. 1 is a schematic diagram showing a medical image-processing apparatus according to a first embodiment.

FIG. 1 is a schematic diagram showing a medical image-processing apparatus according to a first embodiment. FIG. 1 shows a medical image-processing apparatus 10 according to the first embodiment. The medical image-processing apparatus 10 sets a kernel per region, for a phase image that expresses a phase signal of an MR signal by using a method explained below. The medical image-processing apparatus 10 estimates a phase signal caused by a background other than a local phase variation of a tissue by using a kernel of a phase signal, and removes the phase signal of the background from the phase image.

The medical image-processing apparatus 10 is, for example, a special or general purpose computer. Note that the medical image-processing apparatus 10 is only required to be one having a kernel setting function 111 and a background-phase removing function 112 described later. For example, the function of the medical image-processing apparatus 10 can be one that is included in a medical diagnostic imaging apparatus such as an MRI apparatus, a personal computer (PC) (workstation) that subjects a medical image to image processing, a medical image managing apparatus (server) that stores and manages medical images, and the like connected thereto through a network. Explanation is given with a case in which the medical image-processing apparatus 10 is a special or general purpose computer as an example.

Phase images include, in addition to a local phase variation of a tissue, a phase variation caused by a background such as a significant change in magnetic susceptibility caused by air, or non-uniformity in a static magnetic field of an MRI apparatus itself. Therefore, to perform SWI or QSM, the phase variation derived from a background is required to be removed. The background herein signifies, for example, a background magnetic field. That is, to perform SWI or QSM, a phase variation derived from a background magnetic field is required to be removed from a phase image.

Therefore, there is a method of setting a sphere having a predetermined radius as a kernel based on a principle that a phase variation of a background satisfies the Laplace's equation, acquiring a mean value in the sphere as the background, and subtracting the acquired background from a phase image.

However, by such a method, because the type and the size of a kernel is uniform in an entire brain to be a sphere having the same radius, background phases cannot be acquired accurately in an area in which the phase increases, for example, at a boundary between a brain near a paranasal sinus and air, and therefore, the accuracy of a phase image of a tissue is low. Accordingly, the image quality of a phase image is poor.

Therefore, the medical image-processing apparatus 10 according to the first embodiment is configured to improve the image quality of a phase image as explained below. The medical image-processing apparatus 10 includes processing circuitry 11, storage circuitry 12, and an interface (IF) 13.

The processing circuitry 11 signifies an application specific integrated circuit (ASIC), a programmable logic device, or the like, besides a special or general purpose central processing unit (CPU) or a micro-processing unit (MPU). The programmable logic device can be, for example, a simple programmable logic device (SPLD), a complex programmable logic device (CPLD), a field programmable gate array (FPGA), and the like. The processing circuitry 11 reads a program that is stored in the storage circuitry 12, or directly installed in the processing circuitry 11, and executes the read program, thereby implementing the kernel setting function 111 and the background-phase removing function 112.

Moreover, the processing circuitry 11 can be composed of a single circuitry, or of a combination of multiple independent circuitries. In the latter case, the storage circuitry 12 that stores a program can be provided separately for each of the multiple independent circuitries, or a single unit of the storage circuitry 12 can store programs corresponding to respective functions of the multiple independent circuitries.

The processing circuitry 11 implements the kernel setting function 111 and the background-phase removing function 112. The processing circuitry 11 reads various kinds of control programs stored in the storage circuitry 12 to implement the kernel setting function 111 and the background-phase removing function 112, and also controls processing operation of the storage circuitry 12 and the IF 13 collectively.

The kernel setting function 111 is a function of acquiring (reading) a phase image that is stored in the storage circuitry 12, and setting a kernel per region in the phase image. The kernel is to express, for example, a background phase signal that is a phase signal caused by a background other than a local phase variation of a tissue. The kernel setting function 111 is one example of a setting unit.

The background-phase removing function 112 is a function of acquiring a phase image that is stored in the storage circuitry 12, estimating background phases by using a kernel set in each region, and removing the estimated phase of the background from the phase image. The background-phase removing function 112 is one example of a removing unit.

Figure 2:
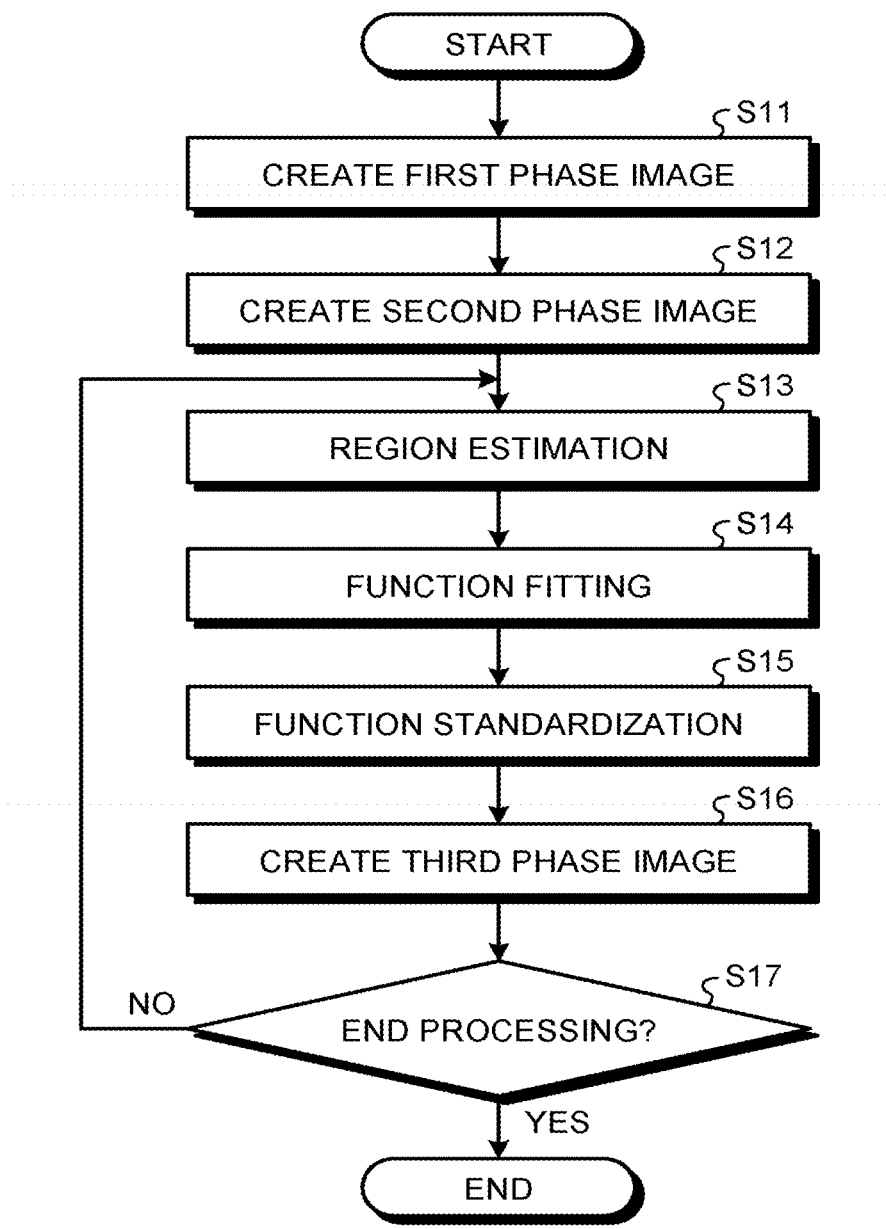
FIG. 2 is a flowchart showing a flow of processing that is performed by the medical image-processing apparatus according to the first embodiment.

Specific explanation of the kernel setting function 111 and the background-phase removing function 112 of the medical image-processing apparatus 10 are given by using a flowchart shown in FIG. 2.

The storage circuitry 12 is implemented by a semiconductor memory device, such as a random access memory (RAM) and a flash memory, a hard disk, an optical disk, or the like. The storage circuitry 12 can be implemented also by a portable media, such as a universal serial bus (USB) memory and a digital versatile disk (DVD). The storage circuitry 12 stores various kinds of processing programs (including an operating system (OS) and the like in addition to application programs) that are used in the processing circuitry 11, data that is necessary for executing the programs, a phase image, and a medical image.

The IF 13 performs communication operation with an external device conforming to a predetermined communication protocol. When the medical image-processing apparatus 10 is provided on a network, the IF 13 performs transmission and reception of information to and from an external device on the network. For example, the IF 13 performs a communication operation with an external device by receiving volume data that is acquired by imaging by a medical diagnostic imaging apparatus (not shown) such as an MRI apparatus from the medical diagnostic imaging apparatus or a medical image managing apparatus (not shown), or by transmitting a three-dimensional image that is generated by the medical image-processing apparatus 10 to a medical image managing apparatus or an interpretation terminal (not shown).

FIG. 2 is a flowchart showing a flow of processing that is performed by the medical image-processing apparatus according to the first embodiment. As a rough flow in the flowchart, first, two types of phase images of a first phase image and a second phase image from which background phases have been removed by a kernel are created (generated). Subsequently, a function that is acquired by performing function fitting on surrounding pixels of a pixel having a large phase that is positioned in a predetermined range of the first phase image is standardized to 0 to 1, and by alphablending using this as an alpha, the first phase image and the second phase image are blended. By such processing, a result of performing background phase removal by a kernel different per pixel is obtained. It is explained below with specific examples.

As shown in FIG. 2, the background-phase removing function 112 removes background phases from a phase image by the SHARP method, and creates the first phase image (step S11). The phase image is a phase image of an MR signal, and is an image having no phase wraparound.

The background-phase removing function 112 then sets a sphere having a smaller radius than a sphere that has been used in the SHARP method, and creates the second phase image regarding a mean value in the sphere as a background (step S12). By setting a sphere having a small radius, background phases can be acquired accurately at an area in which a phase increases at a boundary between a brain around a paranasal sinus and air.

A radius of the sphere set as a kernel at step S11 is different from the radius of the sphere set as a kernel at step S12. That is, size of the kernel (kernel size) set at step S11 is different from size of the kernel set at step S12. A filter adapted the phase image at step S11 is different from a filter adapted the phase image at step S12.

The kernel setting function 111 estimates a region to set a kernel per region (step S13).

Figure 3:
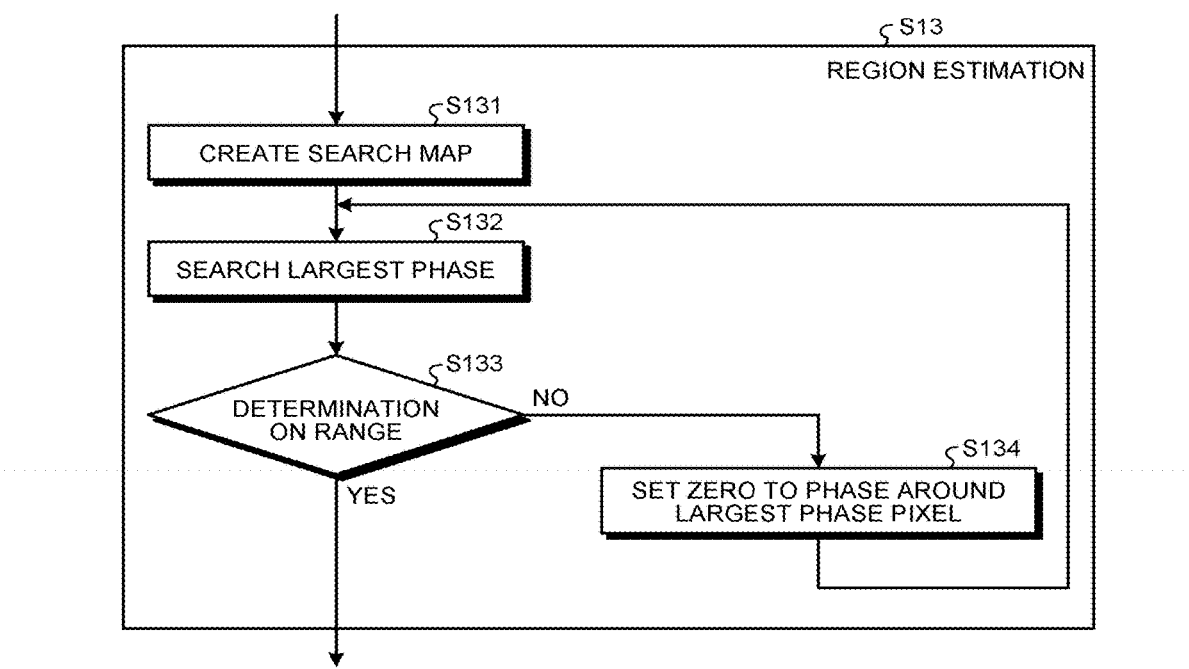
FIG. 3 is a flowchart of region estimation.

FIG. 3 is a flowchart of region estimation. In the flowchart shown in FIG. 3, a pixel, an absolute value of a phase signal of which is large in a predetermined range is searched.

As shown in FIG. 3, the kernel setting function 111 creates a search map from the first phase image (step S131). In this example, a copy of the first phase image is the search map.

The kernel setting function 111 acquires a pixel, an absolute value of a phase of which is the largest from the search map (step S132).

The kernel setting function 111 determines whether the pixel acquired at step S132 is included in a predetermined range (step S133). The predetermined range herein is a range in which background phases cannot be removed sufficiently by the SHARP method, and the range is shown in FIGS. 4A to 4C. FIG. 4A depicts a peripheral area of a paranasal sinus. FIG. 4B depicts a peripheral area of temporal lobes. FIG. 4C depicts a peripheral area of boundaries of a brain. In FIGS. 4A to 4C, "P" indicates a posterior (backward) side of a subject. Furthermore, "A" indicates an anterior (forward) side of the subject. Moreover, "L" indicates the left side of a subject. Furthermore, "R" indicates a right side of the subject. Moreover, "H" indicates an upward side of the subject. Furthermore, "F" indicates a downward side of the subject.

The kernel setting function 111 extracts a three-dimensional region 26 of a brain from the search map by segmentation by threshold processing and the like, region growing, or the like. Subsequently, the kernel setting function ill creates a rectangular parallelepiped (hexahedron) 28, each face of which touches an outline 27 of the region 26 of the brain. The kernel setting function 111 then divides the rectangular parallelepiped 28 into two equal parts in a front-back direction of the subject, into three equal parts in a left-right direction, and into three equal parts in up-down direction. The front-back direction of the subject corresponds to a y direction (fy), the left-right direction corresponds to an x direction (fx), and the up-down direction corresponds to a z direction (fz). Among the 18 three-dimensional regions obtained as a result of division into two equal parts in the front-back direction of the subject, into three equal parts in the left-right direction, and into three equal parts in the up-down direction, the kernel setting function 111 identifies a three-dimensional region 29 positioned at the front in the front-back direction of the subject, in the middle in the left-right direction, and in the middle in the up-down direction as a region around a paranasal sinus. That is, the kernel setting function 111 identifies a region including a paranasal sinus (one example of a part of a subject) of the subject from the search map (copy of the first phase image) based on anatomical information. The anatomical information herein is information indicating that a region of a paranasal sinus of the subject is positioned in the region 29, which is the region at the front in the front-back direction, in the middle in the left-right direction, and in the middle in the up-down direction among the 18 three-dimensional regions that are obtained as a result of dividing the rectangular parallelepiped 28 into two equal parts in the front-back direction of the subject, into three equal parts in the left-right direction, and into three equal parts in the up-down direction. The kernel setting function 111 then determines whether the pixel acquired at step S132 is included in the region 29.

Moreover, as shown in FIG. 4B, the kernel setting function 111 divides the rectangular parallelepiped 28 into four equal parts in the front-back direction of the subject, into three equal parts in the left-right direction, and into two equal parts in the up-down direction. Subsequently, the kernel setting function 111 identifies a three-dimensional region 34 positioned at the third from the front in the front-back direction, at the left in the left-right direction, and at the bottom in the up-down direction as a region around a temporal lobe. Furthermore, the kernel setting function 111 identifies a three-dimensional region 35 positioned at the third from the front in the front-back direction, at the right in the left-right direction, and at the bottom in the up-down direction as a region around a temporal lobe. That is, the kernel setting function 111 identifies a region that includes a temporal lobe (one example of a part of a subject) of the subject from the search map based on anatomical information. The anatomical information herein is information indicating that a region of a temporal lobe of the subject is positioned in the regions 34, 35, which are regions at the third from the front in the front-back direction of the subject, at the bottom in the up-down direction, and at the left and right in the left-right direction among 24 three-dimensional regions that are obtained as a result of dividing the rectangular parallelepiped 28 into four equal parts in the front-back direction, into three equal parts in the left-right direction, and into two equal parts in the up-down direction. The kernel setting function 111 then determines whether the pixel acquired at step S132 is included in either one of the region 34 and the region 35.

Moreover, as shown in FIG. 4C, the kernel setting function 111 creates a distance image of a distance from a background, with the extracted region 26 of the brain as a foreground, and the other region as a background. The kernel setting function 111 then identifies a region 36 that is positioned at a predetermined distance from the background as a region around a boundary of the brain. That is, the kernel setting function 111 identifies a region that includes a boundary of the brain (one example of a part of a subject) of the subject from the distance image created from the search map based on anatomical information. The anatomical information herein is information indicating that the region around a boundary of the brain is a region at a predetermined distance from the background. The region around a boundary of the brain is, for example, a region near the outline 27 (region within a predetermined range from the outline 27) of the region 26 of the brain. The kernel setting function 111 then determines whether the pixel acquired at step S132 is included in the region 36.

The kernel setting function 111 can identify a part of the subject by a similar method from an intensity image that is generated from a magnetic resonance signal based on anatomical information.

When the pixel acquired at step S132 is included in the region 29, the region 34, the region 35, or the region 36 (step S133: YES), that is, when it is determined that further background phase removal is necessary with the pixel acquired at step S132, the kernel setting function 111 estimates a region that is constituted of pixels around the pixel acquired at step S132, and proceeds to step S14.

On the other hand, when the pixel acquired at step S132 is not included in either region (step S133: NO), that is, when background phase removal is not further performed with the pixel acquired at step S132, the kernel setting function 111 sets the phase around the pixel acquired at step S132 in the search map to zero, and returns to step S132 and acquires a pixel, an absolute value of a phase of which is the largest again.

Region estimation is not limited to the method described above. For example, using at least one of the intensity image, the phase image, and the first phase image, patterns per region can be machine-learned to estimate a region. As a specific example, image patterns of four regions of an anterior cranial cavity, middle cranial cavities (left and right), a cerebral falx, and a sinus sagittalis superior, and regions therearound can be learned by extremely randomized trees to be estimated. Alternatively, using at least one image of the intensity image, the phase image, and the first phase image, an atlas in which regions are labeled can be created, to estimate a region by image registration. Alternatively, a region can be estimated by referring to at least one of the intensity image, the phase image, and the first phase image that have been obtained by imaging the same subject in past.

The background-phase removing function 112 performs function fitting on the region estimated at step S13 (step S14). For example, parameters of a three-dimensional generalized Gaussian function are acquired, for example, by the least squares method. Functions and fitting methods used herein are not limited. The function and the fitting method can be selected by a user.

The background-phase removing function 112 standardizes the function to 0 to 1 (step S15).

The background-phase removing function 112 alphablends the first phase image and the second phase image using the function standardized at step S15 as an alpha, to create a third phase image (step S16). In this example, the alphablending is performed such that the third phase image has the phase of the first phase image in a pixel in which the function is 0, and has the phase of the second phase image in a pixel in which the function is 1.

The background-phase removing function 112 determines whether to end the background phase removal (step S17). For example, the background-phase removing function 112 determines whether to end the back ground phase removal by judging whether the background phase removal has reached a specified number. When the background phase removal has reached the specified number, that is, when the background phase removal is to be ended (step S17: YES), the background-phase removing function 112 handles the third phase image as a tissue phase image, and ends the processing.

On the other hand, when the background phase removal has not reached the specified number, that is, when a background phase is to be further removed (step S17: NO), the background-phase removing function 112 handles the third phase image as the first phase image, and returns to step S13 to perform region estimation.

Figure 5:
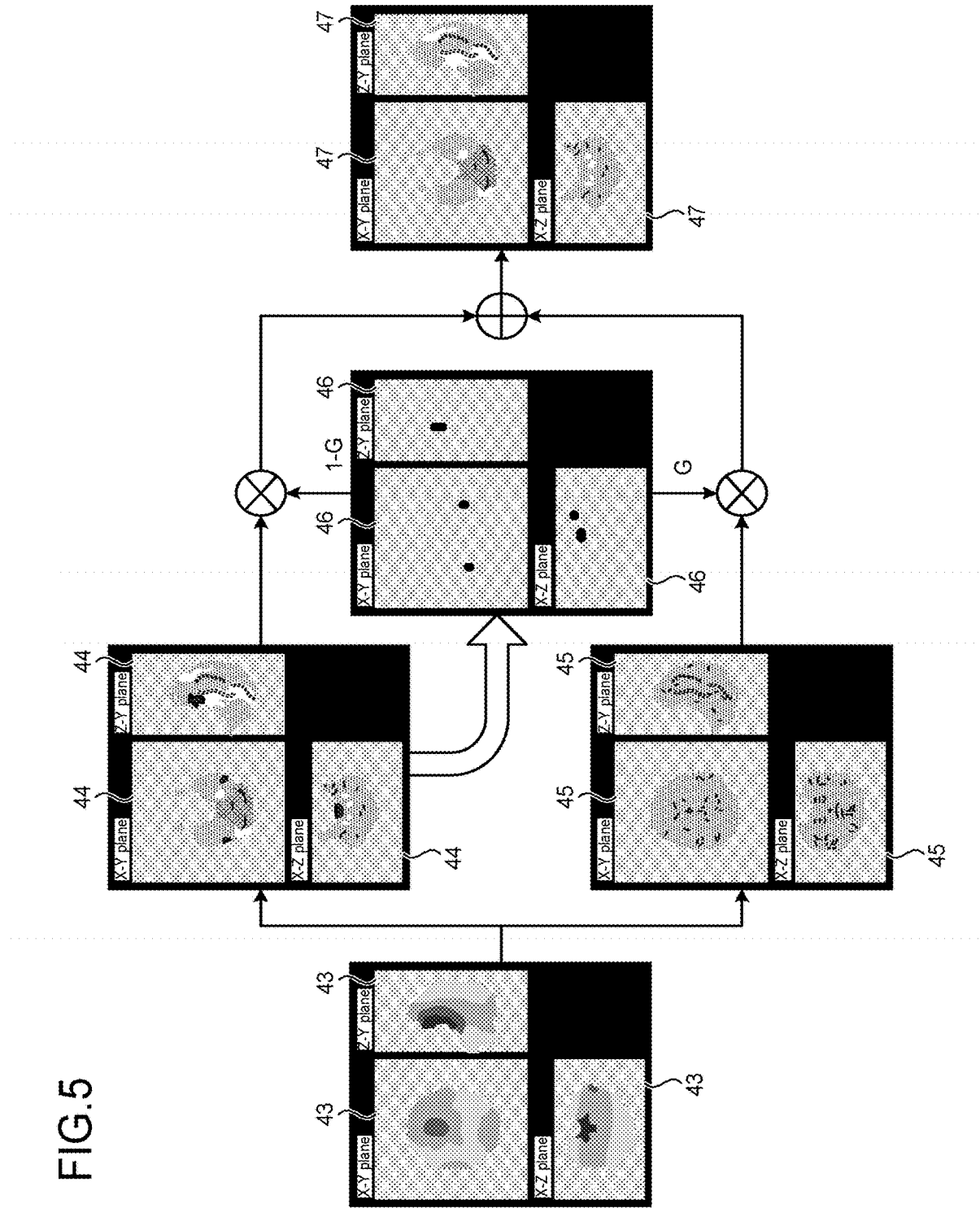
FIG. 5 is a diagram for explaining one example of processing that is performed by processing circuitry according to the first embodiment.

FIG. 5 is a diagram for explaining one example of processing that is performed by processing circuitry according to the first embodiment. In an example shown in FIG. 5, the background-phase removing function 112 removes background phases from a three-dimensional phase image 43 by the SHARP method at step S11, and creates a three-dimensional first phase image 44. In FIG. 5, projection images in which the phase image 43 and the first phase image 44 are projected on each of an fx-fy plane, an fz-fy plane, and an fx-fz plane are shown.

As shown in the example in FIG. 5, at step S12, the function of the background-phase removing function 112 sets a sphere having a radius smaller than that of the sphere use in the SHARP method for the phase image 43, and a mean value in the sphere is removed as a background, to create a three-dimensional second phase image 45. In FIG. 5, projection images in which the second phase image 45 is projected on each of the fx-fy plane, the fz-fy plane, and the fx-fz plane are shown.

As shown in the example in FIG. 5, at step S16, the background-phase removing function 112 alphablends the first phase image 44 and the second phase image 45 using a standardized function (artifact mask) 46 as an alpha, to creates a third phase image 47. In FIG. 5, projection images in which the third phase image 47 are projected on each of the fx-fy plane, the fz-fy plane, and the fx-fz plane are shown.

As explained above, the medical image-processing apparatus 10 according to the first embodiment alphablends the first phase image and the second phase image using a standardized function as an alpha, to create the third phase image. Thus, a result of phase removal of a background having a different kernel size per pixel, that is, a different sphere radius, is applied. As described, the kernel setting function 111 of the medical image-processing apparatus 10 sets a combination of a plurality of filters that are used to remove phase variations caused by a background according to a region in a phase image. The region herein signifies a part based on anatomical information of a subject. The background-phase removing function 112 of the medical image-processing apparatus 10 removes phase variations derived from a background, from a phase image using the kernel. Therefore, the medical image-processing apparatus 10 can improve the accuracy of background phase removal in a portion having a large phase variation, particularly a portion around a paranasal sinus, compared to background phase removal using a sphere of the same radius for an entire image. Therefore, according to the medical image-processing apparatus 10, the image quality of phase images can be improved.

Moreover, in the medical image-processing apparatus 10 according to the first embodiment, the processing circuitry 11 can further include an image creating function, and the image creating function can create a magnetic susceptibility image from the third phase image. There are various methods as a method of creating a magnetic susceptibility image from a phase image. For example, the image creating function creates a magnetic susceptibility image by performing inverse transform on a phase image. As the method using inverse transform, there are various known methods. For example, as a method described in a non-patent document "Quantitative susceptibility Mapping (QSM): Decoding MRI Data for a Tissue Magnetic Biomarker" by Y. Wang et al., Magnetic Resonance in Medicine 73:82-101 (2015), an intensity image can be used for inverse transforming. The MEDI method described in this non-patent document generates a magnetic susceptibility of a tissue highly accurately by a regularization method. Therefore, on the assumption that the intensity image and the magnetic susceptibility image are similar, an outline image is generated from the intensity image, and a final magnetic susceptibility is calculated such that the space continuity of the magnetic susceptibility image is high in a region other than the outline. Note that a method not using an intensity image can also be applied as the method using inverse transform. The image quality of the created magnetic susceptibility image is to be high because the image quality of the third phase image is high. The processing circuitry 11 reads a program that corresponds to the image creating function stored in the storage circuitry 12, and executes the read program, thereby implementing the image creating function.

First Modification According to First Embodiment

Figure 6:
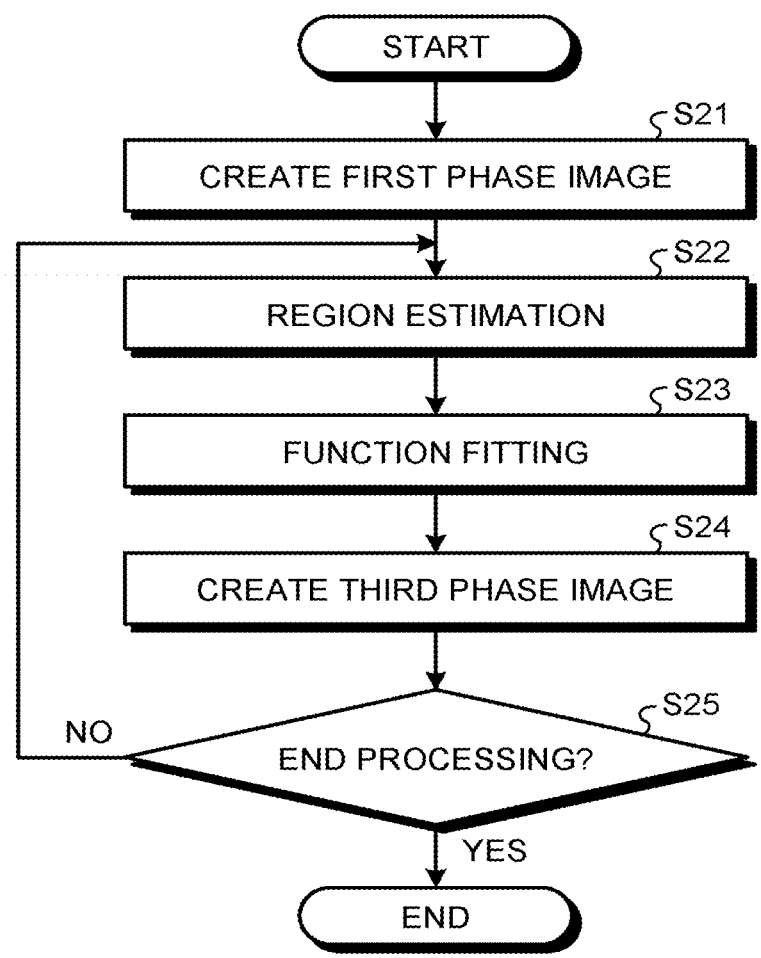
FIG. 6 is a flowchart showing a flow of processing that is performed by a medical image-processing apparatus according to a first modification.

Next, a first modification according to the first embodiment is explained. FIG. 6 is a flowchart showing a flow of processing that is performed by a medical image-processing apparatus according to the first modification. Processing at step S21 shown in FIG. 6 is the same as the processing at step S11 shown in FIG. 2, and processing at step S22 is the same as the processing at step S13. However, by the processing performed by the medical image-processing apparatus 10 according to the first modification, the second phase image is not created.

The background-phase removing function 112 subjects the region estimated at step S22 to function fitting (step S23). For example, parameters of the three-dimensional generalized Gaussian function are acquired, for example, by the least squares method. Functions and fitting methods used herein are not limited.

The background-phase removing function 112 creates the third phase image by subtracting the function acquired at step S23 from the first phase image (step S24). That is, the third phase image includes a pixel from which background phases are removed using a sphere having a radius used by the SHARP method as a kernel, and a pixel from which background phases are further removed using the function that is acquired at step S23 as a kernel. As described, background phase removal results obtained with different kernel sizes and different kernel types per pixel are applied. That is, the medical image-processing apparatus 10 according to the first modification sets a combination of a plurality of filters based on the first phase image that is an intermediate phase image created using one kernel (sphere having a radius used in the SHARP method) out of plural kernels (the sphere having a radius used in the SHARP method and the function). Therefore, the medical image-processing apparatus 10 according to the first modification can improve the accuracy in background phase removal in an area having large phase variations, particularly an area around a paranasal sinus, compared to the background phase removal using a sphere having the same radius in the entire image.

Subsequently, the background-phase removing function 112 determines whether to end the background phase removal (step S25). For example, the background-phase removing function 112 determines whether to end the background phase removal by judging whether the background phase removal has reached a specified number. When the background phase removal has reached the specific number, that is, when the background phase removal is to be ended (step S25: YES), the background-phase removing function 112 handles the third phase image as a tissue phase image, and ends the processing.

On the other hand, when the background phase removal has not reached the specified number, that is, when a background phase is to be further removed (step S25: NO), the background-phase removing function 112 handles the third phase image as the first phase image, and returns to step S22 to perform region estimation.

Figure 7:
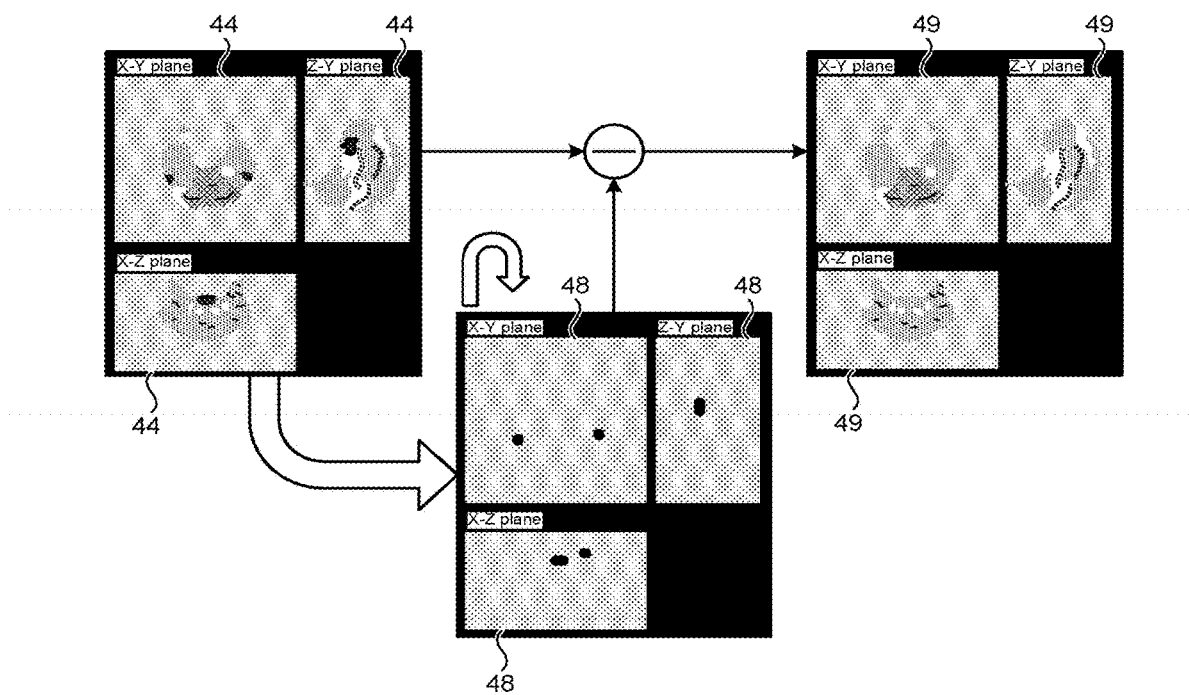
FIG. 7 is a diagram for explaining one example of processing that is performed by the processing circuitry according to the first modification.

FIG. 7 is a diagram for explaining one example of processing that is performed by the processing circuitry according to the first modification. In an example shown in FIG. 7, at step S23, the background-phase removing function 112 subjects the region estimated at step S22 of the first phase image 44 to function fitting.

In the example shown in FIG. 7, at step S24, the background-phase removing function 112 creates a third phase image 49 by subtracting the function acquired at step S23 from the first phase image 44. The respective processing at steps S22 to S24 is repeated until the background-phase removing function 112 determines to end the background phase removal.

The medical image-processing apparatus 10 according to the first modification has been explained. According to the medical image-processing apparatus 10 of the first modification, the image quality of a phase image can be improved as described above.

Second Modification According to First Embodiment

Figure 8:
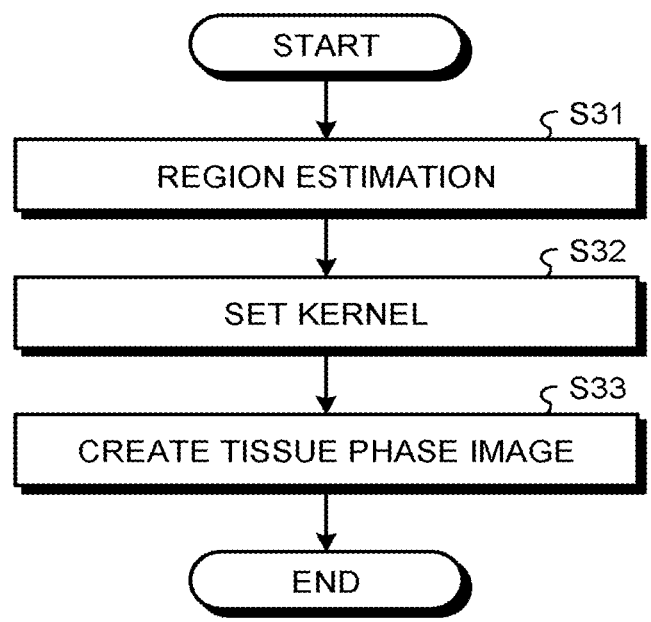
FIG. 8 is a flowchart showing a flow of processing that is performed by a medical image-processing apparatus according to a second modification.

Next, a second modification according to the first embodiment is explained. In the second modification, a kernel is set from a phase image, and a tissue phase image is directly created. FIG. 8 is a flowchart showing a flow of processing that is performed by a medical image-processing apparatus according to the second modification.

The kernel setting function 111 estimates a region by using at least one image out of a phase image and an intensity image (step S31). The estimation method is by machine learning or registration with an atlas, and details of these are as explained in the first embodiment. However, the estimation method is not limited thereto.

The kernel setting function 111 sets a kernel per region (step S32). For example, the kernel setting function 111 uses a sphere having a small radius as a kernel in a portion around a paranasal sinus and a boundary of a brain as shown in FIG. 4A to 4C, and uses a sphere having a radius same as that of the sphere used in the SHARP method is used as a kernel in other areas. The setting method of a kernel is not limited thereto, and the paranasal sinus can, for example set a kernel size, for example, a radius of the sphere, according to a region size per region in a brain, such as a prerubral field, a subthalamic nucleus, a substantia nigra, and the like. For example, the kernel setting function 111 increase the radius of a sphere as the region size increases. That is, the kernel setting function 111 sets the kernel size according to the region size. Moreover, the type of kernel is not limited to a sphere, but can be a circle, a generalized Gaussian function, a frequency filter, and the like. For example, the kernel setting function 111 can set a type of a kernel according to the region size. In addition, the background-phase removing function 112 can be caused to perform background phase removal with various kernel sizes, and a user checks signal change in a tissue phase image of each kernel size, to set a kernel size with which the phase signal significantly changes. For example, the kernel setting function 111 can use different types of kernel in an area around a paranasal sinus or a boundary, and other areas. Furthermore, the kernel setting function 111 can use different sizes of kernel in an area around a paranasal sinus or a boundary of a brain, and other areas. That is, the kernel setting function 111 can set at least one of a kernel size and a kernel type according to a position of a region.

The background-phase removing function 112 creates a tissue phase image by performing background phase removal according to the kernel determined at step S32 (step S33). For example, when the kernel is a sphere, a mean value in the sphere is regarded as a background phase, and when the kernel is a function, a function that is acquired by function fitting is regarded as a background phase. The background-phase removing function 112 then removes the background phase from a phase image, to create a tissue phase image. The of background phase removal method is not limited thereto, and for example, in an area around a boundary of regions, a background phase is estimated by each kernel in a vicinity, and phases of multiple backgrounds are combined by alphablending according to a distance from the region boundary, and the combined phases of multiple backgrounds are removed from the phase image. Thus, discontinuity of phases is avoided to occur at a boundary.

Moreover, an operation to perform background phase removal can be repeated, returning to step S32 at which a kernel is again set for a tissue image per background phase removal.

Second Embodiment

Figure 9:
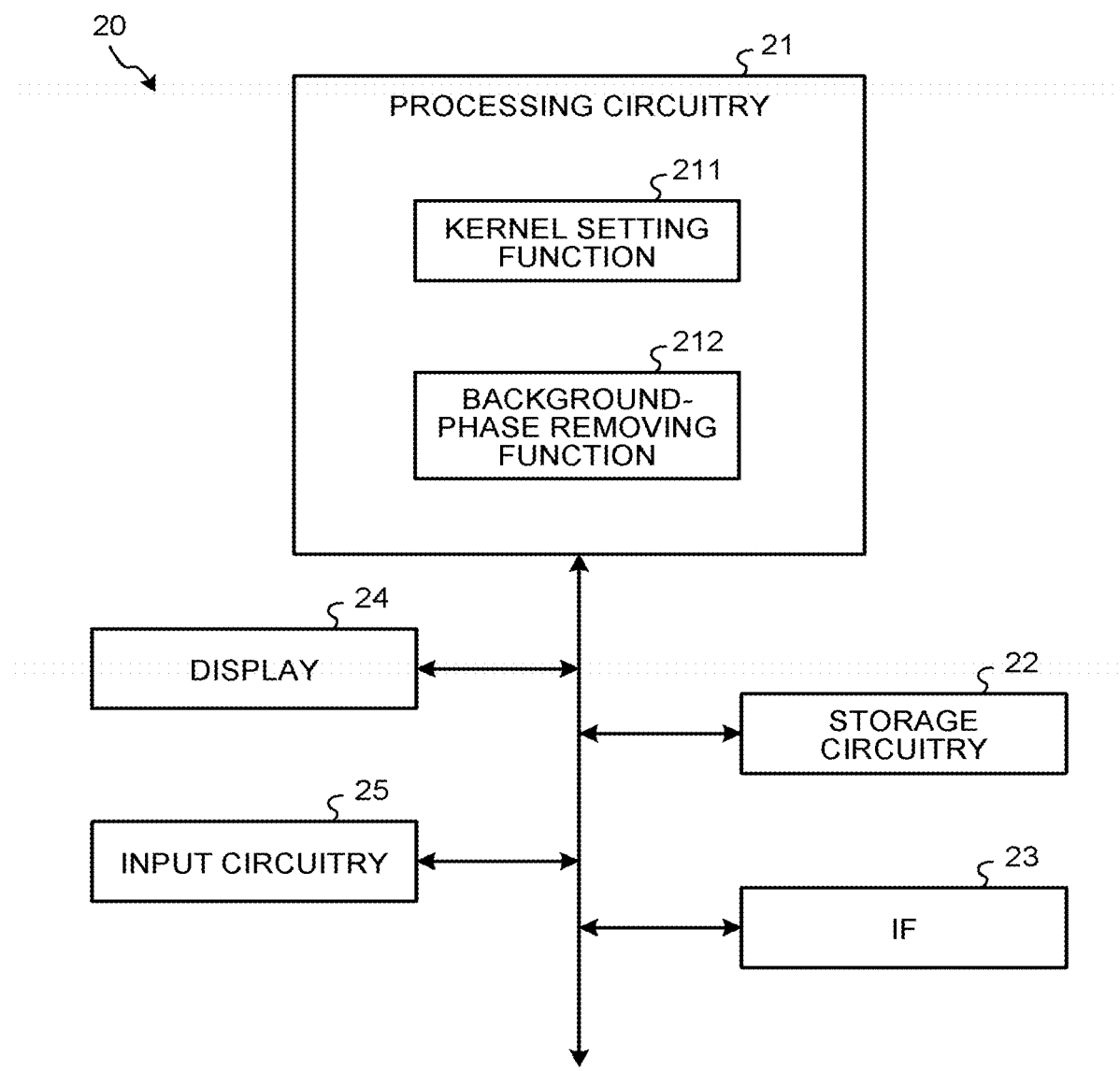
FIG. 9 is a schematic diagram showing a medical image-processing apparatus according to a second embodiment.

FIG. 9 is a schematic diagram showing a medical image-processing apparatus according to a second embodiment. The second embodiment further includes a display 24 and an input circuitry 25 in addition to components of the first embodiment, and enables various kinds of checks and corrections by a user. The storage circuitry 22, and an IF 23 have the same configuration as storage circuitry 12, and the IF 13 above.

The display 24 is constituted of a liquid crystal display (LCD), or the like. The display displays various kinds of operating screens and various display information such as image data on the LCD according to an instruction from processing circuitry 21.

The input circuitry 25 is circuitry to which a signal is input from a pointing device (mouse and the like) or an input device such as a keyboard, that can be operated by a user. In this example, the input device itself is included in the input circuitry 25. When the input device is operated by a user, the input circuitry 25 generates an input signal according to the operation and outputs it to the processing circuitry 21. A medical image-processing apparatus 20 can be equipped with a touch panel that integrates the input device and the display 24 therein.

Figure 10:
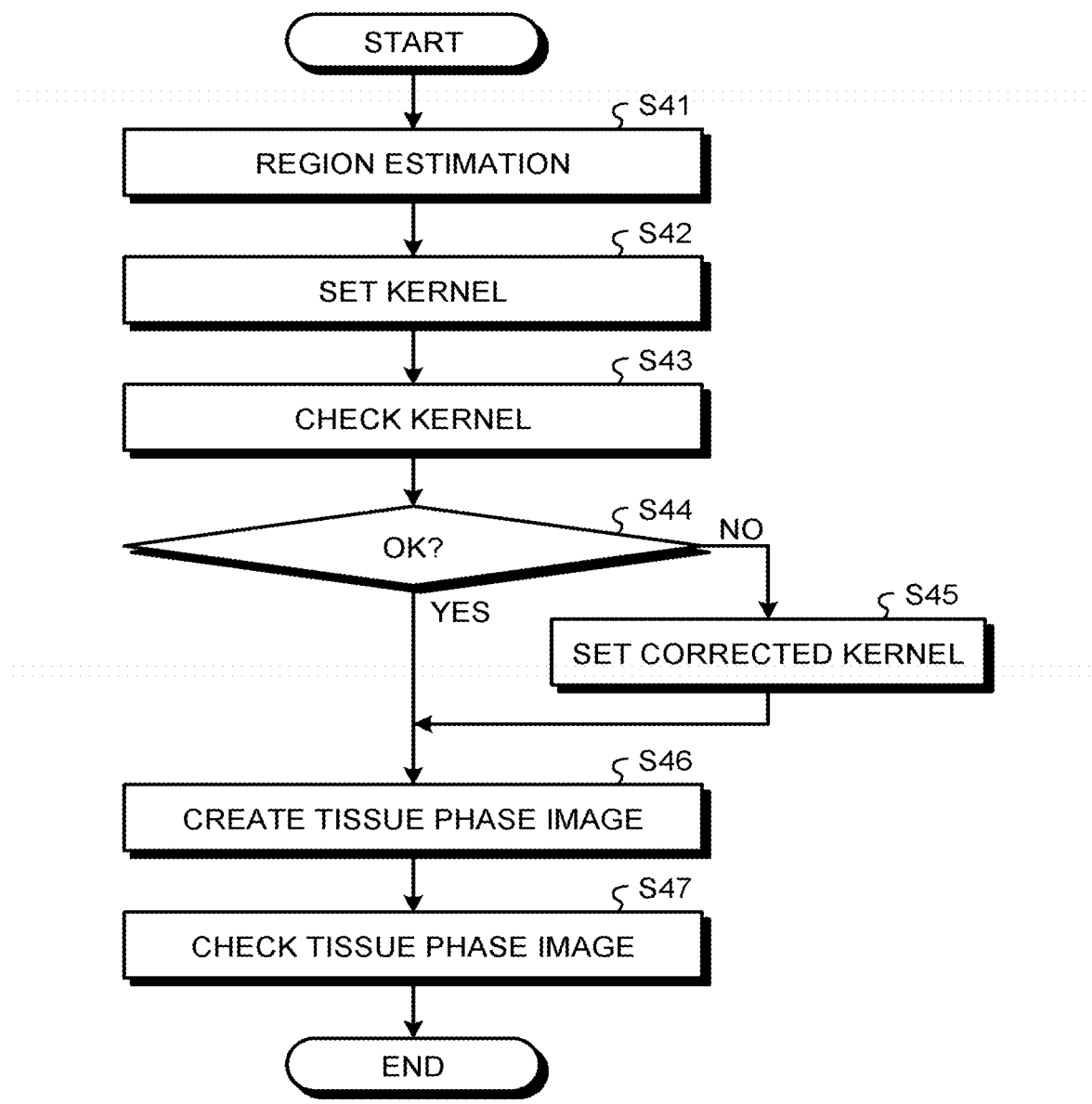
FIG. 10 is a flowchart showing a flow of processing that is performed by the medical image-processing apparatus according to the second embodiment.

FIG. 10 is a flowchart showing a flow of processing that is performed by the medical image-processing apparatus according to the second embodiment. In the second embodiment, a user can check and correct an estimated region, a set kernel size and type, and a tissue phase image as necessary.

Figure 11:
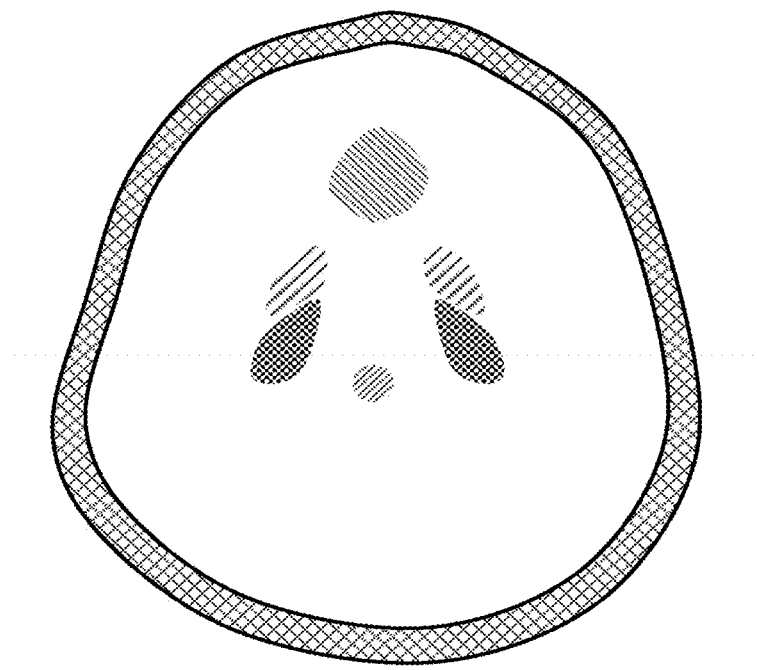
FIG. 11 depicts one example of a display form of a kernel according to the second embodiment.

First, a kernel setting function 211 estimates a region (step S41), and sets a kernel per region (step S42) similarly to the second modification. The kernel setting function 211 then displays a kernel in each region on the display 24, and prompts a user to check it (step S43). FIG. 11 depicts one example of a display form of a kernel according to the second embodiment. As shown in an example in FIG. 11, types and sizes of a kernel is expressed by colors and patterns to be displayed. At step S43, the kernel setting function 211 can display the estimated region on the display 24, to prompt a user to check it. The user checks it, and inputs, when there is no problem in the type and the size of a kernel, an indication that there is no problem in the type and size of a kernel through the input circuitry 25. On the other hand, when at least one of the type and the size is to be corrected, the user selects the region, and corrects the kernel of the selected region.

When the indication that there is no problem is input (step S44: YES), a background-phase removing function 212 creates a tissue phase image similarly to the second modification (step S46), and displays the created tissue phase image on the display 24 to prompt the user to check it (step S47). The user checks it, and inputs an instruction to end the processing through the input circuitry 25 if there is no problem. When correction is to made, the user inputs an indication that the tissue phase image is to be corrected through the input circuitry 25. When the indication that the tissue phase image is to be corrected is input, for example, the background-phase removing function 212 displays both the phase image and the tissue phase image on the display 24. The user compares these images and selects an appropriate phase from either of them through the input circuitry 25. Selection can be done for the entire image, or per region. Alternatively, when the user re-sets a kernel, the background-phase removing function 212 creates a tissue phase image again using this kernel. Note that at least one of step S43 and step S45 can be omitted.

Third Embodiment

Next, a third embodiment is explained. FIG. 12 is a schematic diagram of an MRI apparatus according to a third embodiment. FIG. 12 shows an MRI apparatus 50 according to the third embodiment. The MRI apparatus 50 images a phase image of an MR signal, and removes a background phase signal from the phase image by using a function substantially equivalent to the function explained for the medical image-processing apparatus according to the first embodiment or the second embodiment, to create a tissue phase image.

The MRI apparatus 50 is roughly constituted of an imaging system 51 and a control system 52. The imaging system 51 includes a static magnetic-field magnet 61, a gradient magnetic-field coil 62, a gradient magnetic-field power-supply device 63, a couch 64, couch controlling circuitry 65, a transmitter coil (RF coil for transmission) 66, transmitter circuitry 67, a receiver coils (RF coils for reception) 68*a* to 68*e*, receiver circuitry 69, and a sequencer (sequence controller) 70. The static magnetic-field magnet 61, the gradient magnetic-field coil 62, and the transmitter coil 66 are included in acquiring circuitry that acquires a magnetic resonance signal generated from a subject (patient) P.

The static magnetic-field magnet 61 generates a static magnetic field in a bore (internal space of the static magnetic-field magnet 61), which is an imaging region of the subject P. The static magnetic-field magnet 61 has a superconducting coil therein, and the superconducting coil is cooled to an extremely low temperature by liquid helium. The static magnetic-field magnet 61 generates a static magnetic field by applying an electric current supplied from a power supply for static magnetic field (not shown) in an excitation mode to the superconducting coil, and is disconnected from the power supply for a static magnetic field when thereafter shifted to a permanent magnet mode. The static magnetic-field magnet 61 keeps generating a large static magnetic field for a long time, for example, for one year or longer, once it has shifted to the permanent magnet mode. The static magnetic-field magnet 61 can be constituted of a permanent magnet. The static magnetic-field magnet 61 is one example of a static-magnetic-field generating unit.

The gradient magnetic-field coil 62 is arranged inside the static magnetic-field magnet 61, and is a gradient-magnetic-field generating unit that generates a gradient magnetic field in the internal space. The gradient magnetic-field coil 62 is formed with three coils combined corresponding to respective axes of X, Y, and Z that are perpendicular to each other. These three coils generate a gradient magnetic field, the magnetic field intensity of which vary along the respective axes of X, Y, and Z, receiving a supply of an electric current separately from the gradient magnetic-field power-supply device 63. An X-axis direction is the same direction as the static magnetic field.

The gradient magnetic fields of the respective axes of X, Y, and Z generated by the gradient magnetic-field coil 62 correspond to a gradient magnetic field for read out Gr, a gradient magnetic field for phase encoding Ge, and a gradient magnetic field for slice selection Gs, respectively. The magnetic field for read out Gr is used to change a frequency of an MR signal according to a spatial position. The gradient magnetic field for phase encoding Ge is used to change a phase of an MR signal according to a spatial position. The gradient magnetic field for slice selection Gs is used to determine an imaging section arbitrarily.

The gradient magnetic-field power-supply device 63 supplies an electric current to the gradient magnetic-field coil 62 based on pulse sequence execution data that is transmitted from the sequencer 70.

The couch 64 includes a top panel 64*a* on which the subject P is placed. The couch 64 inserts the top panel 64*a* into a hollow (imaging opening) of the gradient magnetic-field coil 62 in a state in which the subject P is placed thereon, under control by the couch controlling circuitry 65 described later. Usually, this couch 64 is arranged such that a direction of length thereof is parallel to a center axis of the static magnetic-field magnet 61.

The couch controlling circuitry 65 drives the couch 64 under control by the sequencer 70 and moves the top plate 64*a* in the direction of length and the vertical direction. The couch controlling circuitry 65 is implemented by, for example, a processor. The word "processor" herein signifies a circuit, such as an ASIC and a programmable logic device, in addition to a special or general purpose CPU or an MPU.

The programmable logic device can be, for example, a SPLD, a CPLD, an FPGA, and the like.

The transmitter coil 66 is arranged inside the gradient magnetic-field coil 62, and generates an RF pulse by receiving a supply of an RF pulse signal from the transmitter circuitry 67, and applies the RF pulse to the subject P.

The transmitter circuitry 67 transmits an RF pulse signal corresponding to a Larmor frequency to the transmitter coil 66 based on the pulse sequence execution data that is transmitted from the sequencer 70.

The receiver coils 68a to 68e are arranged inside the gradient magnetic-field coil 62, and receive an MR signal that is radiated from an imaging portion of the subject P by an influence of a high frequency magnetic field. The receiver coils 68a to 68e are array coils, each of which has multiple element coils each receiving an MR signal emitted from the imaging portion of the subject, and outputs, when an MR signal is received by each element coil, the received MR signal to the receiver circuitry 69.

The receiver coil 68a is a coil for a head to be mounted at a head portion of the subject P. The receiver coils 68b, 68c are coils for a spine that are arranged between a back of the subject P and the top plate 64a. Moreover, the receiver coils 68d, 68e are coils for an abdominal region that are mounted on an abdominal side of the subject P.

The receiver circuitry 69 generates an MR signal based on the MR signal output from the receiver coils 68a to 68e based on the pulse sequence execution data transmitted from the sequencer 70. Furthermore, when the MR signal is generated, the receiver circuitry 69 transmits the MR signal to the control system 52 through the sequencer 70.

The receiver circuitry 69 has multiple reception channels to receive MR signals that are output from the multiple element coils included in the receiver coils 68a to 68e. When an element coil to be used for imaging is notified by the control system 52, the receiver circuitry 69 assigns a reception channel to the notified element coil so that an MR signal that is output from the notified element coil is received.

The sequencer 70 is connected to the gradient magnetic-field power-supply device 63, the couch controlling circuitry 65, the transmitter circuitry 67, the receiver circuitry 69, and the control system 52. The sequencer 70 stores control information that is necessary to drive the gradient magnetic-field power-supply device 63, the couch controlling circuitry 65, the transmitter circuitry 67, and the receiver circuitry 69, for example, sequence information in which intensity, application duration, and application timing of a pulse current to be applied to the gradient magnetic-field power-supply device 63 are described.

Moreover, the sequencer 70 drives the couch controlling circuitry 65 according to a predetermined sequence stored therein, thereby moving the top plate 64a back and forth in the Z direction relative to a frame. Furthermore, the sequencer 70 drives the gradient magnetic-field power-supply device 63, the transmitter circuitry 67, and the receiver circuitry 69, thereby generating an X-axis gradient magnetic field Gx, a Y-axis gradient magnetic field Gy, a Z-axis gradient magnetic field Gz, and an RF pulse signal in the frame.

The control system 52 performs overall control of the MRI apparatus 50, data collection, image reconstruction, and the like. The control system 52 includes processing circuitry 71, storage circuitry 72, an IF 73, a display 74, input circuitry 75, and image creating circuitry 76.

The processing circuitry 71 includes a kernel setting function 711 and a background-phase removing function 712. The kernel setting function 711 has a function similar to that of the kernel setting function 111 and the kernel setting function 211 described above. Moreover, the background-phase removing function 712 has a function similar to that of the background-phase removing function 112 and the background-phase removing function 212 described above. Therefore, according to the MRI apparatus 50 of the third embodiment, the image quality of a phase image can be improved similarly to the first embodiment and the second embodiment.

The storage circuitry 72, the IF 73, the display 74, and the input circuitry 75 have the same configuration as storage circuitry 22, the IF 23, the display 24, and the input circuitry 25 above. Furthermore, the image creating circuitry 76 creates a phase image based on an MR signal that is generated from the subject P. The phase image is an image to be a subject of processing by the processing circuitry 71. The image creating circuitry 76 is one example of a creating unit. The image creating circuitry 76 can create a magnetic susceptibility image from the third phase image that is obtained by the background-phase removing function 712, similarly to the image creating function described above.

According to at least one of the embodiments and the modifications explained above, the image quality of a phase image can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic-resonance imaging apparatus comprising
    acquiring circuitry configured to acquire a magnetic resonance signal that is generated from a subject; and
    processing circuitry configured to create a phase image based on the magnetic resonance signal, set a combination of a plurality of filters that are used to remove a phase variation derived from a background magnetic field according to a region in the phase image, and remove a phase variation derived from the background magnetic field from the phase image by using the combination of the filters, wherein
    the processing circuitry is configured to
        generate a first phase image and a second phase image from which background phases are removed from the phase image by using two types of filters,
        acquire a function by performing function fitting on the first phase image,
        standardize the function to a value within a predetermined range, and
        generate a third phase image by blending the first phase image and the second phase image by using the value, the third phase image having the phase image from which the phase variation derived from the background magnetic field is removed by using the combination of the filters.

2. The magnetic-resonance imaging apparatus according to claim 1, wherein
    the processing circuitry sets the combination of the filters according to a part based on anatomical information.

3. The magnetic-resonance imaging apparatus according to claim 2, wherein the processing circuitry identifies the part from any one of the phase image and an intensity image that is created from the magnetic resonance signal, based on the anatomical information.

4. The magnetic-resonance imaging apparatus according to claim 1, wherein
the processing circuitry sets the combination of the filters based on an intermediate phase image that is created by using one of the filters.

5. The magnetic-resonance imaging apparatus according to claim 1, wherein
the processing circuitry sets either one of a type and a size of a kernel for each of the filters per region, or both thereof.

6. The magnetic-resonance imaging apparatus according to claim 2, wherein
the processing circuitry sets either one of a type and a size of a kernel for each of the filters per region, or both thereof.

7. The magnetic-resonance imaging apparatus according to claim 1, wherein
the processing circuitry sets a size of a kernel for each of the filters according to at least one of a position and a size of the region.

8. The magnetic-resonance imaging apparatus according to claim 1, wherein
the processing circuitry sets a type of a kernel for each of the filters according to at least one of a position and a size of the region.

9. The magnetic-resonance imaging apparatus according to claim 1, wherein
a type of a kernel for each of the filters is at least either one of a sphere, a generalized Gaussian function, and a frequency filter.

10. The magnetic-resonance imaging apparatus according to claim 1, wherein
the acquiring circuitry includes
a static magnetic-field magnet that generates a static magnetic field;
a gradient magnetic-field coil that generates a gradient magnetic field; and
a transmitter coil that applies a high frequency pulse to a subject.

11. A medical image-processing apparatus comprising processing circuitry configured to acquire a phase image that is created based on a magnetic resonance signal generated from a subject, set a combination of a plurality of filters that are used to remove a phase variation derived from a background magnetic field according to a region in the phase image, and remove a phase variation derived from the background magnetic field from the phase image by using the combination of the filters, wherein
the processing circuitry is configured to
generate a first phase image and a second phase image from which background phases are removed from the phase image by using two types of filters,
acquire a function by performing function fitting on the first phase image,
standardize the function to a value within a predetermined range, and
generate a third phase image by blending the first phase image and the second phase image by using the value, the third phase image having the phase image from which the phase variation derived from the background magnetic field is removed by using the combination of the filters.

12. An image processing method comprising:
acquiring a phase image that is created based on a magnetic resonance signal generated from a subject;
setting a combination of a plurality of filters that are used in combination to remove a phase variation derived from a background magnetic field, according to a region in the phase image; and
removing a phase variation derived from the background magnetic field from the phase image by using the combination of the filters, wherein
the setting comprises generating a first phase image and a second phase image from which background phases are removed from the phase image by using two types of filters, acquiring a function by performing function fitting on the first phase image, and standardizing the function to a value within a predetermined range, and
the removing comprises generating a third phase image by blending the first phase image and the second phase image by using the value, the third phase image having the phase image from which the phase variation derived from the background magnetic field is removed by using the combination of the filters.

* * * * *